United States Patent [19]

Baker

[11] 3,961,640
[45] June 8, 1976

[54] DENTAL HANDPIECE CONTROL
[75] Inventor: Ronald L. Baker, Florence, Ky.
[73] Assignee: Thomas G. Lutes, Fort Mitchell, Ky.; a part interest
[22] Filed: Sept. 23, 1974
[21] Appl. No.: 508,153

[52] U.S. Cl. .................................... 137/87; 32/28
[51] Int. Cl.² ......................................... A61C 1/05
[58] Field of Search ............ 251/295, 25; 137/636, 137/636.1, 87, 111; 32/28

[56] References Cited
UNITED STATES PATENTS

| | | | |
|---|---|---|---|
| 3,129,511 | 4/1964 | Williams | 32/28 |
| 3,237,306 | 3/1966 | Staunt | 32/28 |
| 3,875,958 | 4/1975 | Miller | 137/87 |

Primary Examiner—Robert G. Nilson
Attorney, Agent, or Firm—Wood, Herron & Evans

[57] ABSTRACT

A dental handpiece control in which a single housing for controlling the flow of air and water to a dental handpiece is combined with a foot pedal. In the housing is a pressure regulator directly operated by the foot pedal and a water valve controlled by air from the pressure regulator. A switching valve operated by push buttons adjacent the foot pedal controls the flow of air to the water valve, the operation of the push buttons determining whether the handpiece is operated on an air mode or an air/water mode. The water valve is designed to eliminate drip when the instrument is shut off by drawing water from the handpiece toward the control unit upon relief of air pressure from the water valve.

10 Claims, 2 Drawing Figures

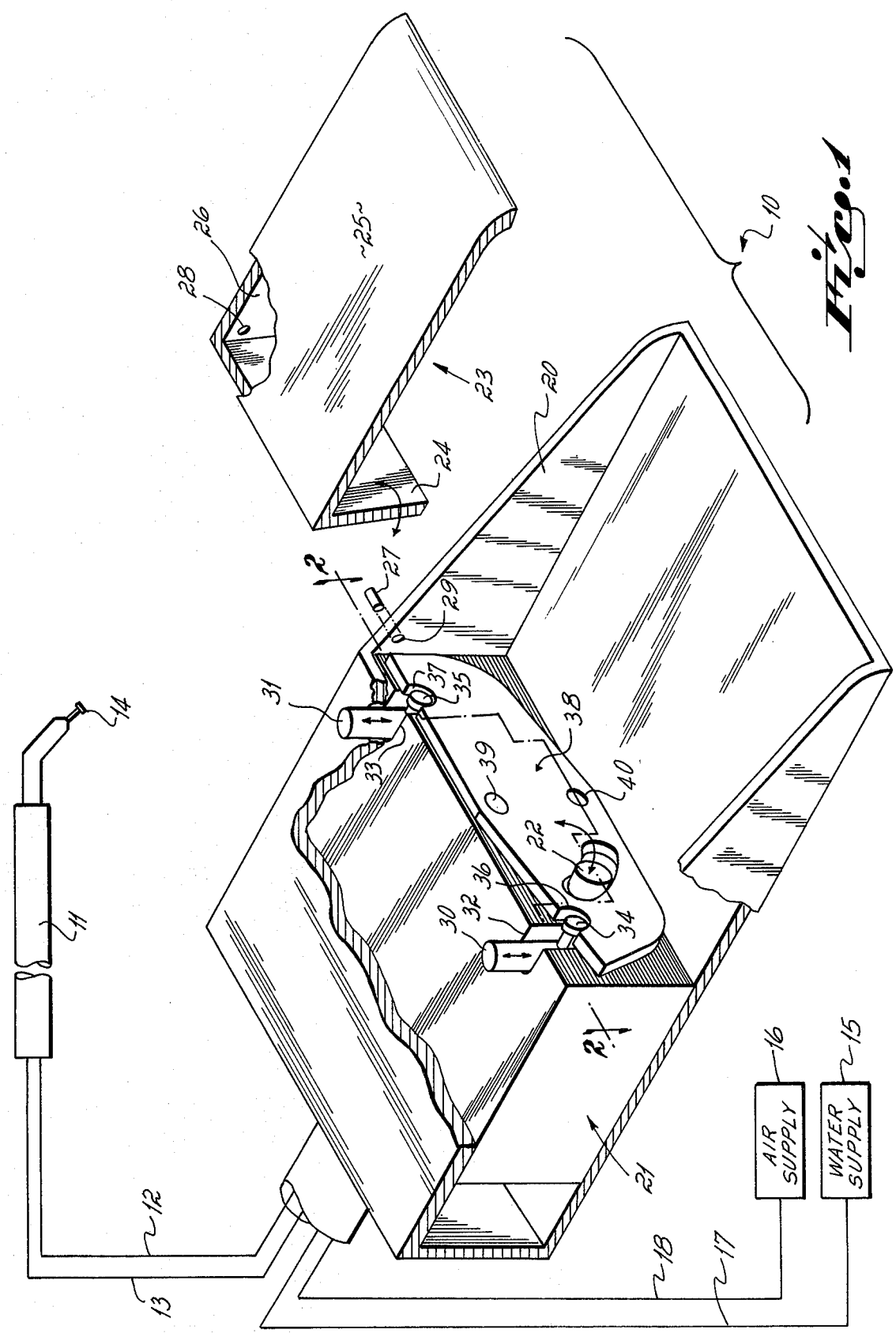

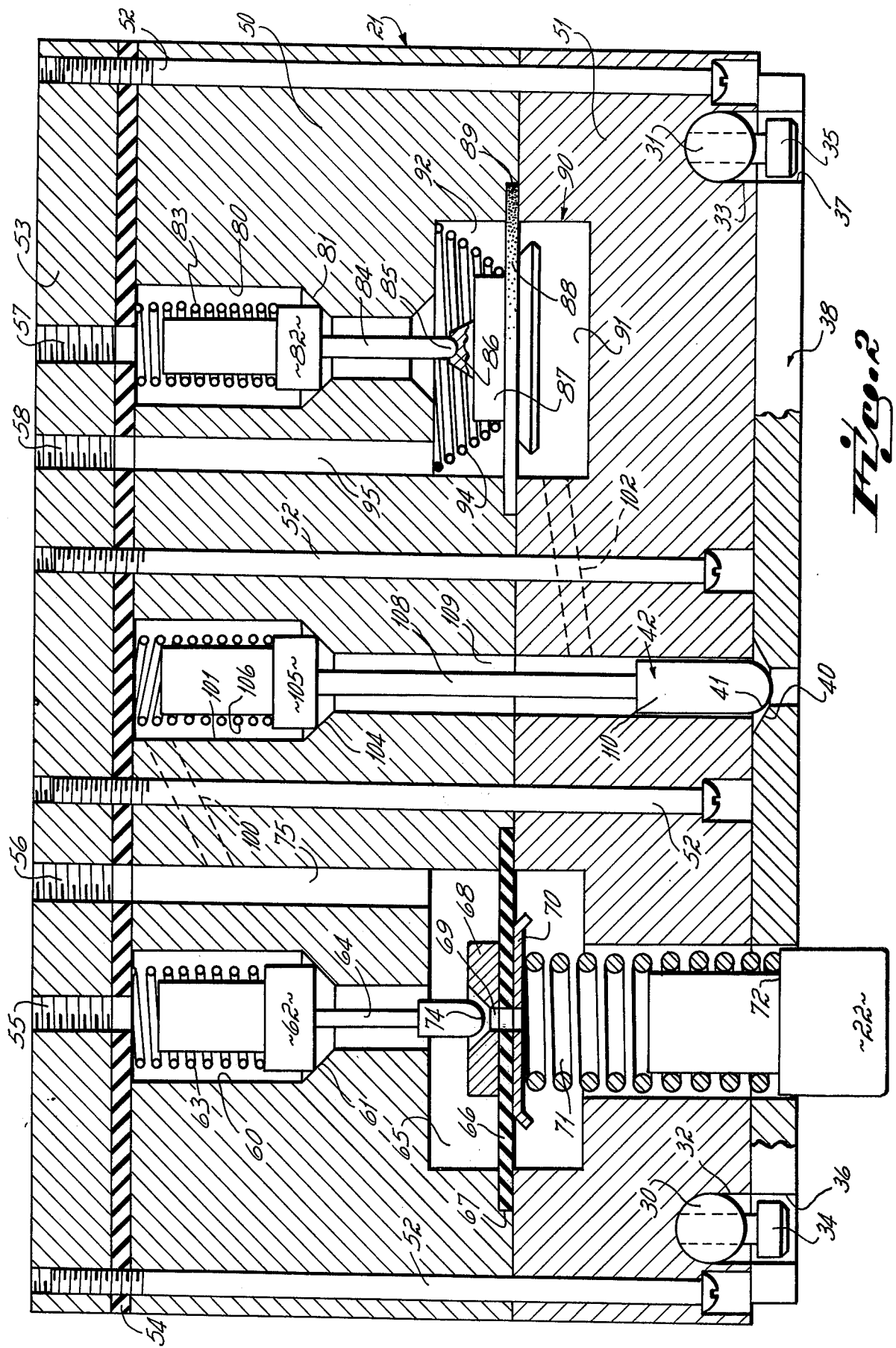

DENTAL HANDPIECE CONTROL

This invention relates to a foot-operated control for a dental handpiece. Since about the mid-1950's the preparation of teeth for filling has been done with a dental handpiece which is a high speed air-operated drill. The burrs are mounted in an air-operated rotor and the speed of the rotor, up to several hundred thousand rpm, is controlled by controlling the flow of air to the handpiece. In addition to supplying and controlling air to the handpiece, it has been the practice to provide a small flow of water to the handpiece, the water acting as a coolant to the tooth during its preparation.

The handpiece with its air and water supplies is normally operated in one of two different modes, depending upon the particular phase of the preparation of the tooth. In one mode air and water are supplied simultaneously, the water cooling the tooth as the air causes the rotation of the handpiece rotor. In the other mode, the water is shut off, the air mode being employed, for example, in the final preparation of the tooth where it is desired to have the tooth dry for the receipt of the filling material.

The controls for the air and water supplies have been and are of differing types. Some controls employ two pedals, one pedal for air and the other for the air/water mode. Some controls employ a control unit separate from the foot pedals, the control unit having valves for the supply of water and air, the foot pedals controlling those valves either electrically or otherwise. In still another type of unit, the foot pedals control the size of the orifice through which the air is supplied to the handpiece so that the dentist does not, through his foot, sense any change in the pressure at which the air is supplied to the handpiece. In this system the sensing of the speed at which the handpiece is operated is done primarily by the sound of the handpiece.

An objective of the present invention has been to provide a single compact control unit associated directly with a single foot pedal, the control unit having the following features:

a. A single foot pedal to control the speed of the rotor in the handpiece and selector buttons adjacent the foot pedal to determine the mode, air or air/water, of operation of the handpiece.

b. A pressure regulator directly operable by the foot pedal to control the supply of air to the handpiece, the pressure regulator and foot pedal combination permitting the dentist to "feel" through the change of pressure on the foot pedal, the speed at which the handpiece is operated.

c. Provision for immediate shut off of the water to the handpiece and withdrawing it away from the handpiece upon cessation of the operation of the handpiece.

These features of the invention are obtained by providing in a single housing to which a foot pedal is mounted a pressure regulator to control air supply, a water valve which is opened by applying air pressure to it and a push button-operated valve to control the supply of air to the water valve. Further, the water valve is designed so that upon relief of the pressure which operates it, a water chamber which is in communication with tubing to which the handpiece is connected is enlarged to withdraw water from the handpiece a short distance down the tubing toward the water chamber. Thus, water dripping from the handpiece following cessation of its operation is eliminated.

It can be seen from the foregoing that all of the handpiece functions are controllable by a single unit combined with the foot pedal. Further, the single foot pedal permits the dentist to be sensitive to the pressure at which the handpiece is operated as well as eliminating any inadvertent shift to the wrong mode of operation because of a failure to depress the proper foot pedal.

The several features of the invention and their advantages will become more readily apparent from the following detailed description taken in conjunction with the accompanying drawings in which:

FIG. 1 is a perspective view partially disassembled and partially in section illustrating the control of the present invention, and FIG. 2 is a cross sectional view taken along lines 2—2 of FIG. 1.

As shown in FIG. 1, the foot-operated control 10 is connected to a dental handpiece 11 through flexible tubing 12 and 13 through which air and water, respectively, flow. The handpiece is of a well known design in which a rotatable member 14 is caused to rotate by means of air under pressure passing through the handpiece. The handpiece has ports (not shown) adapted to discharge water so that a tooth can be cooled during its preparation.

The water and air come from supplies 15 and 16, respectively, through tubing 17 and 18. The tubing 17 and 18 is connected to the control 10 and the flow of the respective fluids to the handpiece is regulated by the control 10.

The control 10 has a casing 20 in which a housing 21 or control body is mounted. A push button 22 connected to a pressure regulator within the housing projects from said housing and is operable by an L-shaped lever 23 having a vertical leg 24 which engages the push button and a generally horizontal leg 25 which is engageable by the foot of the operator. The lever 23 has side walls 26 by which the lever is pivoted to the casing 20, the lever being pivoted on the casing 20 by pins 27 passing through aligned holes 28 and 29 in the lever and casing respectively.

The control has, projecting from the casing 20, an air button 30 and an air/water button 31. If the air button is depressed, the control is set for air only to the handpiece. If the air/water button 31 is depressed, the control is set for air and water to the handpiece. The buttons are slidably mounted in slotted bores 32, 33 in the housing and have lugs 34, 35 projecting laterally from them. The lugs engage grooves 36, 37 in a cam plate 38 which is pivoted on a bolt 39 threaded into the housing. The cam plate has a recess (FIG. 2) 40 forming a cam surface which is engageable with a follower surface 41 on a stem 42 slidably mounted in the housing. As viewed in FIG. 1, pivoting the cam plate in a counterclockwise direction causes the follower surface to drop into the recess, placing the control in an air only mode. Depressing button 31 causes the cam plate 38 to rotate in a clockwise direction, camming the stem 42 into the control causing the control to operate on an air/water mode.

The position of the cam plate 38 only selects the mode of operation. The operator is required to depress the lever or foot pedal 23 to open the valves in the control which permit the flow of either air or air and water to the handpiece. Thus, once the mode is selected, the operator will know that the operation of the handpiece will continue in that mode until he takes the affirmative act of depressing one of the buttons 30-31 to change the mode, thereby avoiding an inadvertent shift from one mode to another.

Referring now to FIG. 2, the housing 21 includes a block 50 having a cap 51 secured to one side by eight bolts 52. The bolts 52 pass through the cap 51 and block 50 and are threaded into a plate 53 secured to the other side of the block. A gasket 54 is clamped between the plate 53 and block 50. The plate 53 contains an air inlet port 55, an air outlet port 56, a water inlet port 57 and a water outlet port 58. These ports are connected by suitable fittings to the tubing 12, 13, 17 and 18 to interconnect the air and water supplies with handpiece 11.

The block 50 has a bore 60 communicating with air inlet port 55 and presenting a frusto-conical valve seat 61. An axially movable closure member 62 is located in the bore and is engageable with the valve seat to open and close the bore 60. A compression spring 63 bears against the closure member 62 and the gasket 54 to urge the closure member toward closed position.

A valve stem 64 secured to the closure member 62 projects into a circular chamber 65. A diaphragm 66 has its peripheral edges 67 clamped in the housing between the body 50 and the cap 51. A vent seat 68 having a central bore 69 is mounted on the diaphragm 66 and is secured to a washer 70 on the opposite side of the diaphragm. A compression spring 71 bears against the washer 70 at one end and is engaged at the other end by a shoulder 72 on the push button 22. The vent seat 68 is normally spaced from the end 74 of the stem 64, thereby permitting the escape of air from the chamber 65 through the bore 69 when the pressure on the push button 22 is relieved.

When pressure on the foot pedal and hence push button 22 is applied, the diaphragm 66 is flexed inwardly to bring the vent seat 68 into engagement with the end 74 of the stem, thereby sealing off the bore 69. Continued movement of the diaphragm against the stem 64 causes the closure member 62 to move away from the seat 61, thereby opening the air valve to admit air from the air supply through the port 55, bore 60, chamber 65 and out through a bore 75 to the air outlet port 56. The high pressure air, that is, air above atmospheric pressure, will act on the diaphragm 66 and hence the spring 71, tending to compress the spring 71 to permit the air valve to close. Movement of closure member 62 will relieve the pressure, thereby maintaining the valve open. A balance between the two reactions will be achieved at a desired air pressure which is determined by the extent to which the button 22 is depressed. That pressure will be directly felt by the dentist.

The water valve in the control includes a bore 80 connected to the water inlet port 57. The bore 80 has a frusto-conical surface 81 providing a valve seat which is engageable by a closure member 82. The closure member 82 is urged by a spring 83 into closed position against the seat 81. The closure member 82 has a stem 84 having an end 85 which normally rests in a recess 86 in a block 87 secured to a diaphragm 88. The diaphragm is clamped around its edges 89 between the block 50 and cap 51 and divides a cavity 90 formed between aligned recesses in the block 50 and cap 51 into an air chamber 91 and a water chamber 92.

A compression spring 94 is seated against one surface of the water chamber and bears against the diaphragm 88 normally causing it to flex slightly into the air chamber 91. The water chamber 92 is connected to a bore 95 in communication with the water outlet port 58.

It can be seen that when the diaphragm 88 flexes toward the valve seat 81, the engagement of its block 87 with the valve stem 85 will force the closure member 82 from the valve seat 81, thereby permitting water to pass from the inlet port 57 through the bore 80, the water chamber 92, the bore 95 and out through the port 58 to the handpiece.

The water valve is operated by air pressure from the air supply being admitted into the air chamber 91. For that purpose a passageway between the air bore 75 and the air chamber 91 is formed by a transverse bore 100, a bore 101 and a transverse bore 102 connecting the bore 101 to the air chamber 91. The bore 101 has a frusto-conical section 104 forming a valve seat which is engageable by a closure member 105, the closure member being urged by a compression spring 106 located between the closure member and the gasket 54 into closed position. The closure member is integral with the elongated stem 42 which has the cam surface portion 41 at its end which is projectable outside the surface of the housing 21 and engageable by cam plate 38 to effect its axial movement. The stem 42 has a smaller diameter section 108 between the closure member 105 and the passageway 102, thereby providing a large space 109 between the bore 101 and the stem 108. The stem has a large diameter section 110 at its end between the passageway 102 and the outer surface of the housing. That large diameter section is of smaller diameter than the portion of the bore 101 within which it slides so as to permit air slowly to vent through the small space between the bore and the large diameter section 110. That space could be airtight as by providing an O-ring in the bore 101 and the stem could be made into two pieces with the piece disposed in the cap 51 having a small bore for venting purposes. Still further venting could be eliminated altogether, although venting is desirable for one condition of operation, as will be explained below.

It can be seen that when the cam plate 38 is rotated to cam the valve stem 42 inwardly, the closure member 105 will be moved off the seat 104, thereby permitting air under pressure from the port 75 to flow through the transverse bore 100, the bore 101 and the transverse bore 102 into the air chamber 91. That air under pressure will cause the diaphragm 88 to flex toward the valve seat 81, thereby lifting the closure member off the valve seat. Thus, water will be permitted to flow from the inlet port 57 to the outlet port 58 as described above.

The water under pressure in the flexible resilient tubing 13 will cause the hoses to distend. When the valve is thereafter closed, the tubing will tend to contract, tending to cause the water to drip undesirably out of the handpiece. To eliminate that drip, provision is made for continued movement of the diaphragm 88 toward the air chamber 91 after the closure member 82 has engaged the seat 81 to cut off the supply of water. That continued movement is caused at least in part by the compression spring 94. In that continued movement, the block 87 on the diaphragm 88 moves away from the stem 85 under the pressure of the spring 94 or the resilience of the diaphragm, thereby enlarging the water chamber 92 after the water valve has been shifted to closed position. The enlargement of the chamber 92 draws water from the tubing 13 toward the water chamber 92, thereby avoiding the drip through the handpiece after it has been shut off.

As the diaphragm 88 flexes toward the air chamber 91, the air in the air chamber 91 is vented through the bores 102, 101, 100, 75 and out of the bore 69 in the diaphragm 66.

If during a water/air mode of operation the air button is depressed to shift to an air mode of operation without relieving the pressure on the push button 22, the closure member 105 would move against its seat without first having permitted air under pressure in the air chamber and associated ports to have been relieved through the bore 69. Under this condition, the diaphragm 88 would tend to remain under pressure, leaving the water valve open. However, with the venting between the stem 42 and the bore 101, the air pressure in the chamber 91 can be relieved to permit the water valve to close.

In the normal operation of the invention, the dentist selects the mode of operation as, for example, by depressing the air/water button 31. Thereafter, when he is ready to begin the preparation of the tooth, he depresses the foot pedal 23 causing the button 22 to move into the housing. Air is available at the inlet port 55 at, for example, 60 to 80 psi. The air at the outlet port 56 will be under that pressure determined by the extent to which the valve 62 is open, that is, the extent to which closure member 62 is spaced from the seat 61. That distance is in turn determined by the pressure which the dentist applies to the foot pedal, the greater the pressure the greater the extent to which the valve is open. As the air pressure at the outlet 56 is increased, the rotatable member in the handpiece will increase its rotary speed. Thus, the dentist can "feel" through the pressure on the foot pedal the speed at which he wishes to operate his instrument.

The water valve may be set to open at, for example, 5 psi. Thus, when the air pressure is sufficient to operate the handpiece, it will be sufficient to open the water valve through the bores which form the passageway between the bore 75 and the air chamber 91. As explained above, that passageway will have been opened by depressing the air/water button 31 which in turn rotates the cam plate 38, camming the valve stem 42 inwardly to open the valve.

When pressure on the foot pedal is relieved, the air valve will be closed through the urging of the spring 63. Relief of the air pressure, through the bore 69 in the diaphragm 66, will relieve all of the pressure in the system, thereby permitting the water valve to close upon the urging of the spring 83. As the water valve closes, the diaphragm 88 continues to flex into the air chamber 91 under the pressure of spring 94, thereby withdrawing water via bore 95 from the tubing to the handpiece.

When the mode of operation is to be changed to air only, push button 30 is depressed to rotate the cam plate 38, thereby permitting the valve stem 42 to shift axially into the recess 40 as urged by the spring 106. Thus, the passageway from the air side of the control to the air chamber 91 is closed. Depressing the foot pedal 23 urges the push button 22 inwardly which in turn moves the diaphragm 66 into engagement with the air valve stem 64 to open the air valve. Upon opening the air valve, air flows through the bore 60 to the bore 75 and out of the air port 56 to the handpiece.

I claim:

1. A control for regulating the supply of water and air to a dental handpiece comprising,
    a housing,
    an air inlet port and an air outlet port in said housing,
    an air valve interconnecting said air ports,
    an operator for said air valve having a portion projecting from said housing,
    a water inlet port and a water outlet port in said housing,
    a water valve interconnecting said water ports,
    a fluid pressure operator for said water valve,
    an air passageway connected between said air outlet port and said fluid pressure operator to operate said water valve when said passageway is open and high pressure air is at said air outlet port,
    a valve in said passageway,
    and means on said housing for opening and closing said passageway valve.

2. A control as in claim 1 in which said air valve operator includes,
    a diaphragm supported at its edges in a bore,
    means connecting said diaphragm to said valve to open said valve when said diaphragm is flexed toward said valve,
    means connecting said projecting portion to said diaphragm to flex said diaphragm toward said valve upon application of pressure on said projecting portion.

3. A control as in claim 1 in which said air valve operator includes,
    a diaphragm supported at its edges in a bore communicating with said air inlet port,
    said diaphragm having a central bore,
    a valve stem projecting from said air valve toward said diaphragm, said valve stem normally being spaced from said diaphragm and being engageable by said diaphragm to open said air valve and close said port,
    and means connecting said projecting portion to said diaphragm to flex said diaphragm toward said valve upon application of pressure on said projecting portion.

4. A control as in claim 1 in which said passageway valve includes a stem having a follower surface projecting outside said housing,
    said opening and closing means comprising a cam plate mounted on said housing for movement between open and closed positions,
    a cam surface on said plate cooperating with said follower surface to cam said stem into said housing to open said valve,
    and spring means normally urging said valve to a closed position wherein said stem projects out of said housing.

5. A control as in claim 1 in which said passageway valve includes means to vent said passageway upon closure of said passageway valve.

6. A control as in claim 1 in which said fluid pressure operator for said water valve comprises,
    a chamber in said housing,
    a diaphragm secured at its edges in said housing and dividing said chamber into a water chamber adjacent said water valve, and an air chamber on the opposite side thereof,
    said diaphragm being operably connected to said water valve to open said water valve upon introduction of high pressure air into said air chamber, said passageway being connected to said air chamber.

7. A control as in claim 6 further comprising,
a spring in said chamber urging said diaphragm toward said air chamber whereby, upon relief of air pressure, said diaphragm will be flexed toward said air chamber to draw water into said water chamber.

8. A control as in claim 6 further comprising,
a lost motion connection between said diaphragm and said water valve, and a spring urging said diaphragm to flex into said air chamber, whereby as said air valve is closed said diaphragm will flex into said air chamber and withdraw water into said housing through said water outlet port.

9. A control as in claim 1 in which said water valve operator comprises,
a diaphragm secured at its peripheral edge in said housing,
means connecting said diaphragm to said water valve,
an air chamber in said housing on one side of said diaphragm, said air chamber connected to said passageway whereby air under pressure in said passageway and air chamber will cause said diaphragm to flex toward said water valve to open said water valve.

10. A control unit for a dental handpiece comprising,
a housing,
air, middle and water bores in said housing,
a valve seat and cooperating closure member in each said bore,
an operator for said air closure member projecting outside said housing,
a diaphragm controlled operator for said water closure member,
a passageway connecting said air bore through said middle bore to said diaphragm, and
an operator for said middle closure member projecting outside said housing for selectively controlling the operation of said diaphragm when said air closure member operator is actuated.

* * * * *